United States Patent [19]
Forrester et al.

[11] Patent Number: 5,376,555
[45] Date of Patent: Dec. 27, 1994

[54] METHOD FOR TESTING BREATH ALCOHOL WITH DISCRIMINATION BETWEEN ALVEOLAR AND UPPER RESPIRATORY TRACT ALCOHOL

[75] Inventors: Glenn C. Forrester, Oakland; Roger Allen, Benicia; Roger Herrera, Oakland, all of Calif.; Daniel S. Goldberger, Boulder, Colo.; James R. Braig, Oakland, Calif.

[73] Assignee: Intoximeters, Inc., St. Louis, Mo.

[21] Appl. No.: 202,282

[22] Filed: Feb. 25, 1994

[51] Int. Cl.$^5$ .................. G01N 21/61; G01N 33/497
[52] U.S. Cl. ..................... 436/132; 436/133; 436/900; 422/84; 128/719; 73/23.3
[58] Field of Search ............. 436/52, 68, 131, 132, 436/133, 164, 171, 181, 900; 422/84; 128/719, 730; 73/1 G, 23.21, 23.3; 250/340, 343, 344, 345; 364/497, 498, 499

[56] References Cited

U.S. PATENT DOCUMENTS

| | | | |
|---|---|---|---|
| 3,830,630 | 8/1974 | Kiefer et al. | 422/84 X |
| 4,090,078 | 5/1978 | Heim | 422/84 X |
| 4,268,751 | 5/1981 | Fritzlen et al. | 250/343 |
| 4,314,564 | 2/1982 | Albarda | 128/719 |
| 4,363,635 | 12/1982 | Hutson | 422/84 X |
| 4,736,619 | 4/1988 | Legrand | 422/84 X |
| 5,048,321 | 9/1991 | Chow | 422/84 X |

Primary Examiner—Jeffrey R. Snay
Attorney, Agent, or Firm—Polster, Lieder, Woodruff & Lucchesi

[57] ABSTRACT

A method and infrared sensing device for determining the concentration of alveolar alcohol in a breath sample exhaled by a subject into an infrared sensing device. The presence of alcohol from the upper respiratory tract of the subject is detected by continuously monitoring alcohol and carbon dioxide, normalizing alcohol values with respect to carbon dioxide, calculating a difference between normalized alcohol concentration and carbon dioxide concentration over time, integrating (summing) the difference, and comparing the integrated difference with a threshold. This technique accurately and consistently detects the presence of mouth alcohol in the sample before the presence of carbon dioxide which originates in deep lung breath.

6 Claims, 4 Drawing Sheets

METHOD FOR TESTING BREATH ALCOHOL WITH DISCRIMINATION BETWEEN ALVEOLAR AND UPPER RESPIRATORY TRACT ALCOHOL

FIELD OF INVENTION

This invention relates to the quantitative determination of the concentration of alcohol in a human breath sample for the purpose of determining blood alcohol concentration.

BACKGROUND OF THE INVENTION

In testing breath alcohol to determine blood alcohol (ethanol) concentrations, pure deep lung breath or alveolar breath is the part of a breath sample which best reflects the actual blood alcohol concentration of the subject at the time of testing. In current commercially available breath alcohol testing devices various methods are used to insure that the portion of the breath sample that is analyzed is deep lung breath which is uncontaminated by extraneous residual alcohol in the subject's mouth or upper respiratory tract.

When a subject exhales, his or her breath initially comes primarily from the mouth and upper respiratory tract. As exhalation continues, the breath predominantly comes from the deep lungs or alveoli.

When a subject who has not recently ingested alcohol exhales, the profile of alcohol concentration in his or her breath is characterized by a rapid increase in the concentration of alcohol present, leveling off to a plateau as the breath sample becomes pure deep lung (alveolar) breath. An instrument which continuously measures alcohol concentration during exhalation, such as an infrared detector, produces an output such as shown in FIG. 1 for such a subject. This phenomenon is well known, and by identifying the level of the alcohol concentration plateau a reliable determination of blood alcohol concentration can be made.

The accurate determination of alveolar alcohol can be complicated, however, by the presence of alcohol in the patient's upper respiratory tract ("mouth alcohol"). When a subject who has recently ingested alcohol breathes into an instrument which continuously measures alcohol concentration, the output profile is characterized by a more pronounced and rapid increase in the sample's alcohol concentration followed by a decrease in the indicated alcohol concentration as shown in FIG. 2. The conventional way to determine the presence of mouth alcohol is to measure the output of the detector during the entire exhalation of a subject's breath, to look for this characteristic peak in the indicated concentration of alcohol, and to reject the sample if this peak is present.

It is known to those skilled in the art that this approach is not entirely reliable. As the amount of mouth alcohol present declines, the characteristic peak in alcohol concentration becomes less and less apparent until, at lower levels, mouth alcohol is completely indistinguishable from deep lung alcohol. Another difficulty arises when a subject with a large amount of alcohol in his or her upper respiratory tract provides a slow and steady breath sample. It is possible that the residual alcohol in such a subject never gets completely flushed from the upper respiratory tract and no peak ever occurs. The characteristic peak in alcohol concentration from mouth alcohol in both of these cases is further obscured by the presence of actual blood alcohol in the deep lung air.

SUMMARY OF THE INVENTION

One of the objects of this invention is to provide a device and method for reliably detecting the presence of mouth alcohol in a subject's breath sample, irrespective of the amount of mouth alcohol, the amount of alveolar alcohol, or the way in which the subject blows into the measuring instrument.

Other objects will be apparent to those skilled in the art in light of the following description and accompanying drawings.

In accordance with one aspect of this invention, generally stated, a method of determining the concentration of a measured alveolar gas in a breath sample exhaled by a subject into a sensing device is improved by a discrimination method for determining the presence in the sample of the same gas from the upper respiratory tract of the subject, the discrimination method comprising a step of taking a plurality of measures of the measured gas and a second gas over a period of time, the second gas being known to have a substantially higher concentration in alveolar breath than in either ambient air or upper respiratory breath, early measures of the measured gas and the second gas representing upper respiratory breath and later measures representing deep lung breath, and a step of determining if concentration of the measured gas rises before concentration of the second gas. In the preferred embodiment, the measured gas is alcohol (ethanol), the second gas is carbon dioxide, and the measuring instrument includes an infrared cell wherein the electromagnetic energy generated by a source at one end of the cell is absorbed by molecules of alcohol and other substances before reaching one or more infrared detectors at the other end of the cell. The diminishment of signal from the detector or detectors is measured to determine the concentration of alcohol and other substances present at a given point in time.

The present method is based on the observation what mouth alcohol (or other measured gas) will be present in the breath sample before any substance that diffuses into the alveolar gas space of the lungs from the blood, while alveolar alcohol (or other measured gas representative of that gas's concentration in blood) will be present concurrently with any other substance that is present in the alveolar gas space. By selecting a reference gas having an elevated concentration in the alveoli but not in the upper respiratory tract, a reliable method is provided for determining the presence of the measured gas in the upper respiratory tract. Carbon dioxide is a highly convenient reference gas because its concentration in ambient air is low (on the order of 0.035%) and its concentration in alveolar air is high (about 4.5 to 5.5%) because elevated concentrations come only from the alveoli, and because it is easily discriminated in an infrared detector. In the preferred embodiment, if during exhalation alcohol is detected before carbon dioxide is detected, then that alcohol must have come from a part of the respiratory tract other than the alveoli and does not represent true blood alcohol levels. Preferably, a measurement which includes mouth alcohol is discarded and the measurement is made again after about a ten-minute wait for the level of mouth alcohol to decrease to a negligible level.

In the preferred embodiment and in accordance with a preferred device for carrying out the method, the infrared cell is made up of a source and three detectors:

an ethanol channel, a carbon dioxide channel and a reference channel. The reference channel, although not necessary to make an accurate determination of mouth alcohol, is very helpful in quantifying the concentration of the substances present in the sample. The outputs of the ethanol and carbon dioxide channels are monitored continuously and the output of the reference channel is factored out from the ethanol and carbon dioxide signals to produce the respective output curves of concentration against time in accordance with Beer's law.

In the preferred embodiment of the present invention, at least one of the carbon dioxide profile and the ethanol profile of a given sample is mathematically scaled and offset so that both share the same baseline value and maximum value. The carbon dioxide profile is then subtracted from the ethanol profile, producing a third curve. The presence of mouth alcohol is indicated by a peak exceeding a threshold. This approach has been found to yield consistent and correct determinations of the presence of alcohol in the upper respiratory tract of the subject. The threshold valise for a positive determination is chosen to factor out such interferences as noise in the instrument circuitry and the ethanol that would normally be found in the saliva in the upper respiratory system of an intoxicated subject.

Other aspects of the invention are best understood in light of the description of the preferred embodiment.

DESCRIPTION OF THE PREFERRED EMBODIMENT

Figure 1:
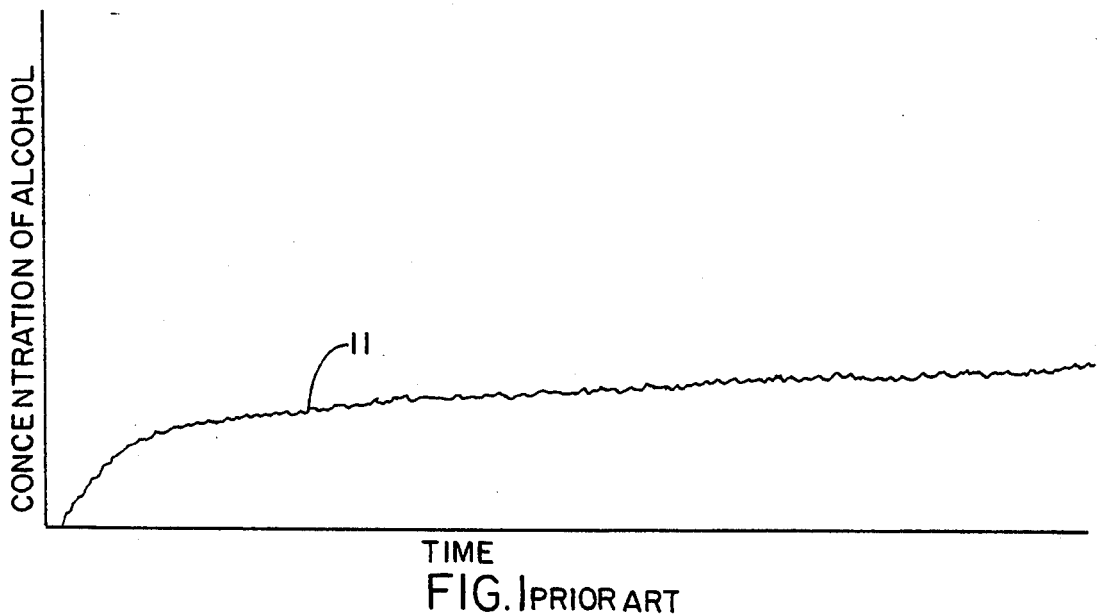
FIG. 1 is a graph of alcohol concentration over the duration of a breath sample from a subject with a blood alcohol content (BAC) of 0.100.

Referring now to the drawings, as previously discussed FIG. 1 is a graphical representation of the output of a commercially available infrared breath alcohol detector, showing the output 11 for a subject having a 0.100 BAC who has not ingested an alcoholic beverage for a considerable period of time. The X-axis of the graph shows time, which is typically three to ten seconds; the Y-axis shows calculated alcohol concentrations. No interfering mouth alcohol is present, and the instrument provides an accurate reading of alveolar breath alcohol based on the value of the curve at its right-hand end.

Figure 2:
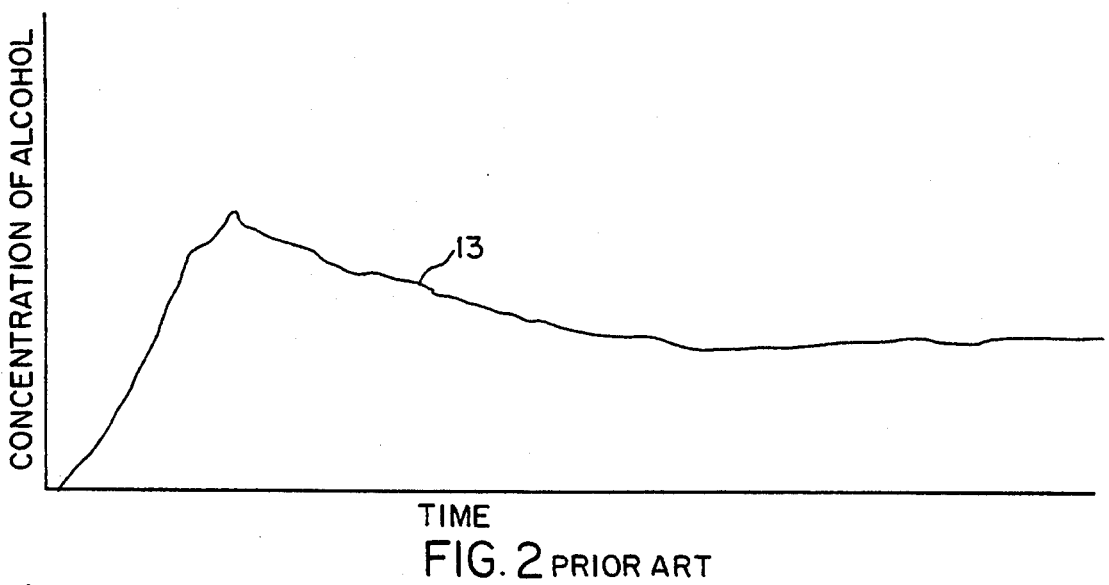
FIG. 2 is a similar graph of a breath sample from a subject with a 0.100 BAC who had ingested an alcoholic beverage thirty seconds before giving the breath sample.
Figure 3A:
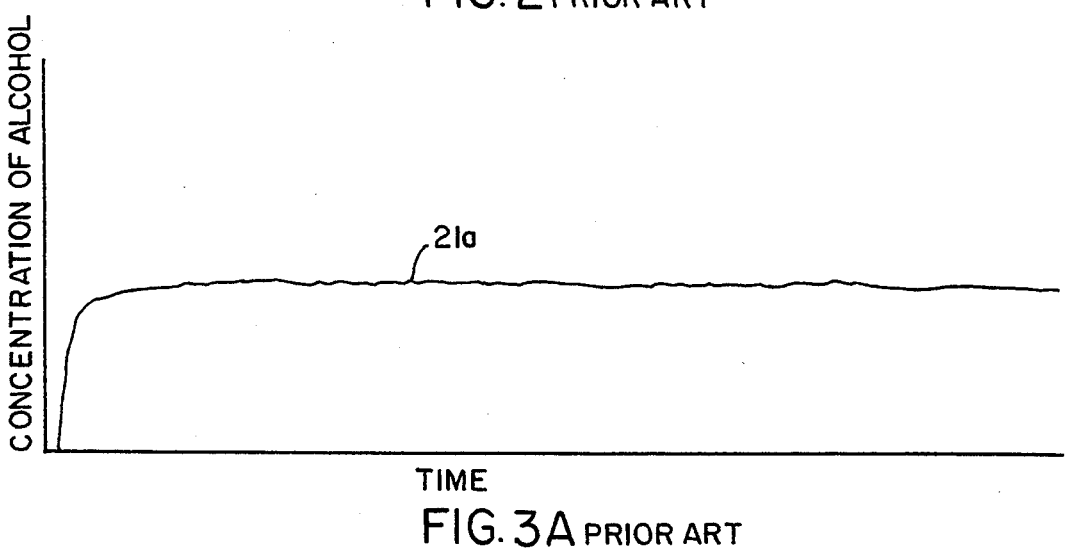
FIGS. 3a–3d are graphs, similar to FIG. 2, of alcohol concentration over the duration of a breath sample from a single subject with a 0.056 BAC, one, three, five and fifteen minutes after ingesting an alcoholic beverage.
Figure 3B:
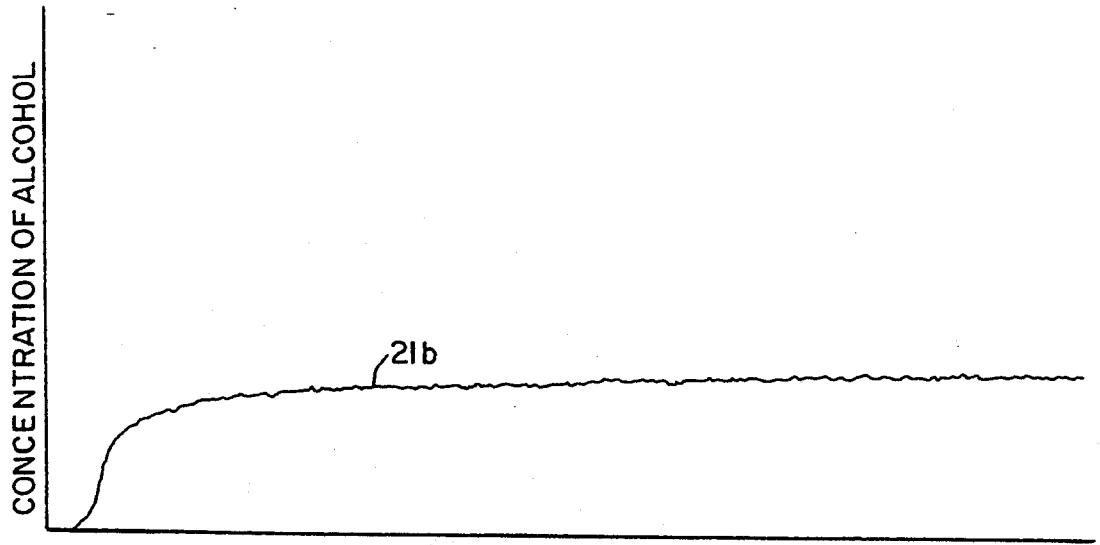
Figure 3C:
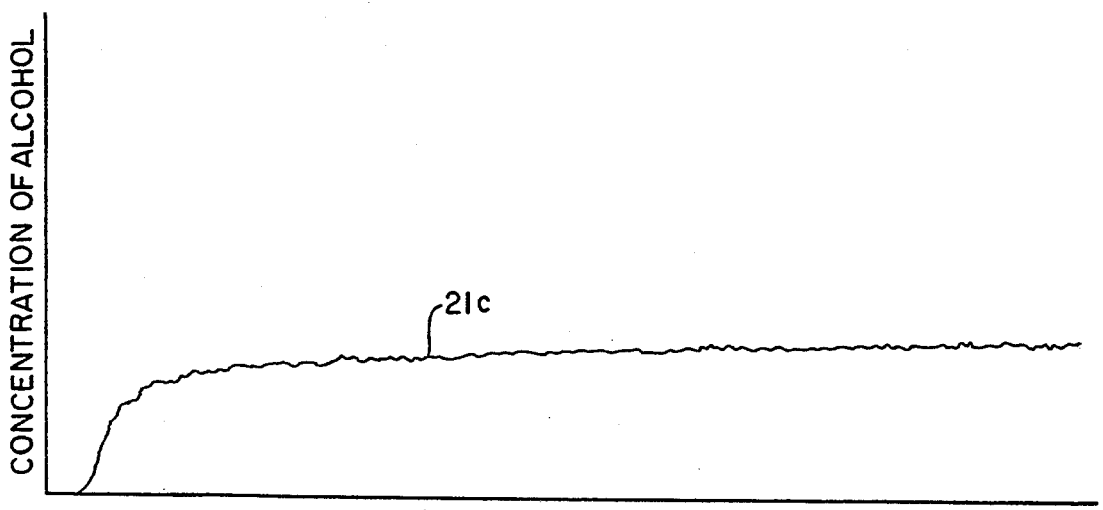
Figure 3D:
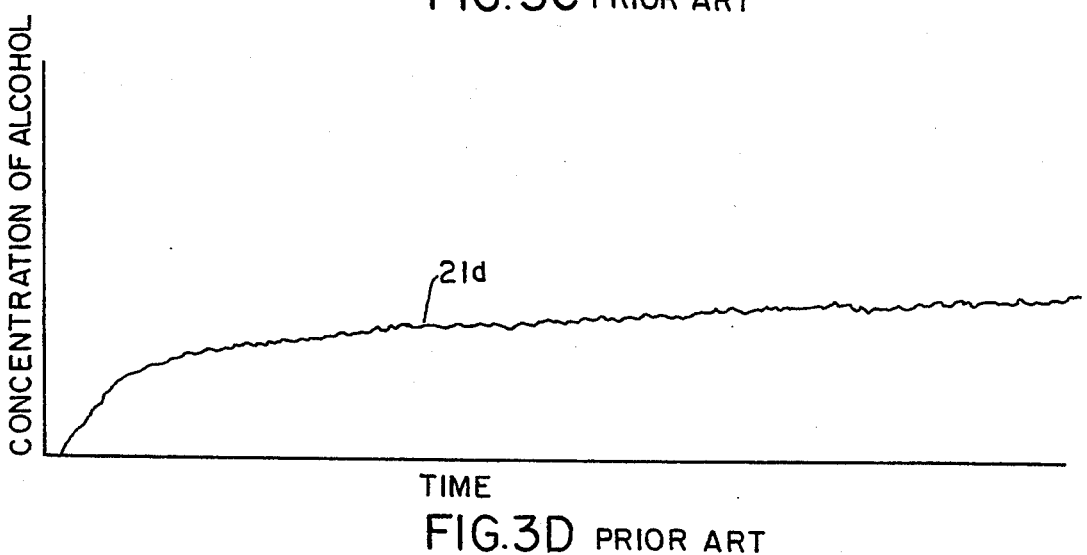

FIG. 2 is a similar graphical representation of the breath alcohol profile 13 produced by the same instrument of a subject with a 0.100 BAC who had ingested an alcoholic beverage thirty seconds prior to giving the breath sample. The classic mouth alcohol peak is detectable by most operators using such a commercially available infrared-based alcohol breath testing apparatus.

FIGS. 3a–3d represent similar graphical representations of the breath alcohol profiles 21a, 21b, 21c, and 21d produced by such an instrument of a single subject with a 0.056 BAC who had ingested an alcoholic beverage one, three, five, and fifteen minutes, respectively, prior to giving the breath sample. These profiles do not show the classic mouth alcohol peak and would not be identified as mouth alcohol by the operator of commercially available infrared devices. Therefore, the concentration of alcohol in the subject's blood would be overestimated in the first three instances. The amount of error would be considerable in the first case (curve 21a), and would be not insignificant in the case of curves 21b and 21c. Curve 21d represents only deep lung alcohol and is therefore an accurate reflection of blood alcohol concentration. The present invention provides a means for identifying that curves 21a–21c include mouth alcohol and alerting the user of an infrared breath testing device that the results of those test are not reliable reflections of blood alcohol concentration.

Figure 4:
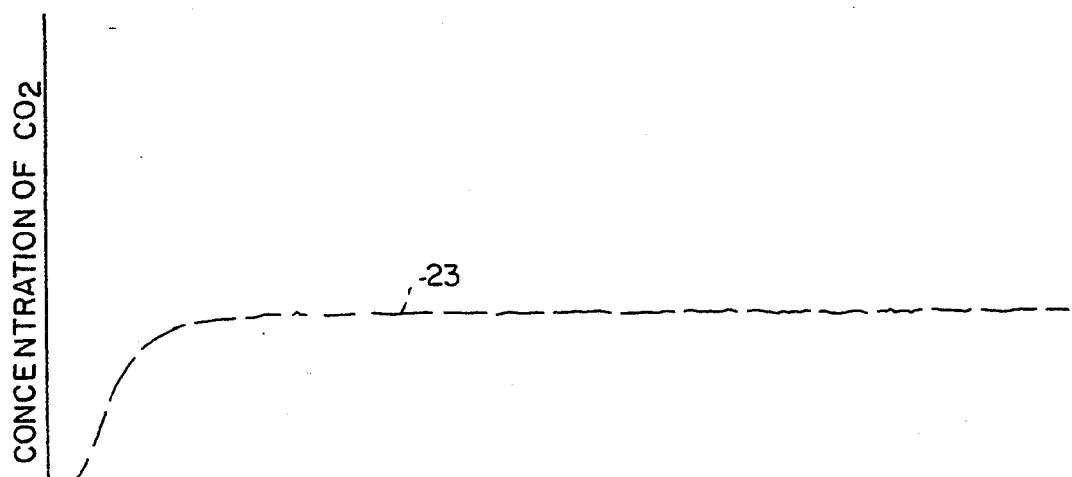
FIG. 4 is a graph of a typical carbon dioxide concentration profile over the duration of a breath sample from a subject.

As shown in FIG. 4, in accordance with the present invention carbon dioxide in the subject's exhaled breath is also monitored each time a measurement of breath alcohol is made and a profile 23 is made. Carbon dioxide concentration varies little (less than a factor of two) from subject to subject and increases greatly in alveolar breath. It ms therefore a convenient alveolar gas to measure.

Figure 5A:
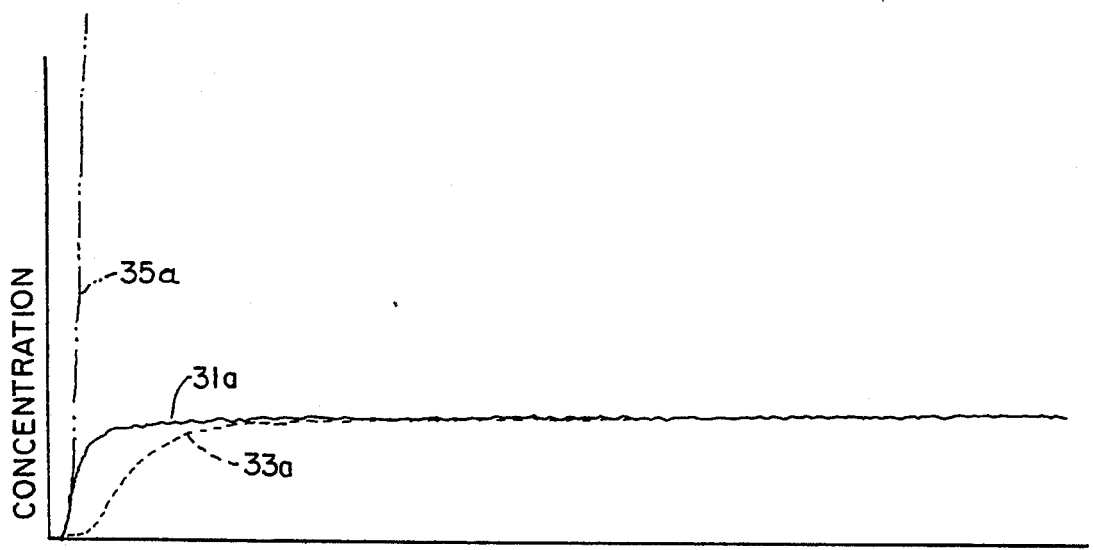
FIGS. 5a–5d are graphs of the same samples as FIGS. 3a–3d, showing the corresponding carbon dioxide profiles of the samples, the alcohol profiles normalized (offset and scaled) and superimposed on the carbon dioxide profiles, and a third curve generated by subtracting the carbon dioxide curve from the alcohol curve.
Figure 5B:
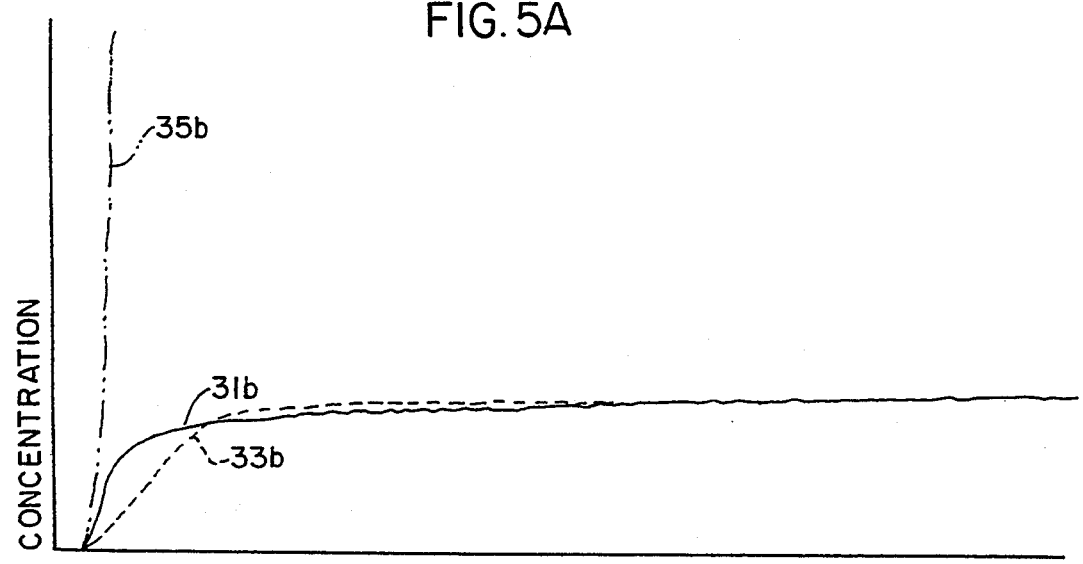
Figure 5C:
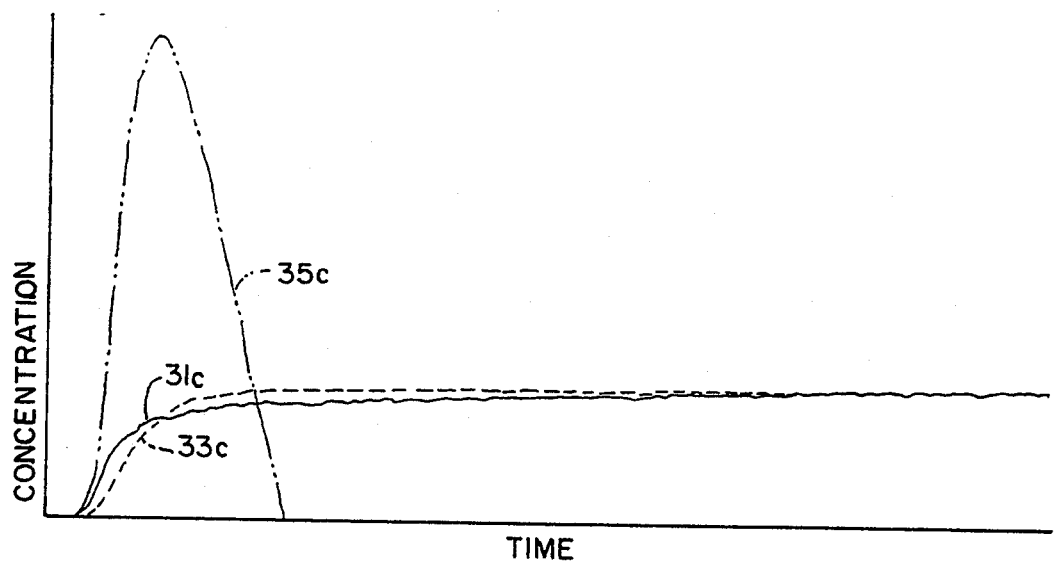
Figure 5D:
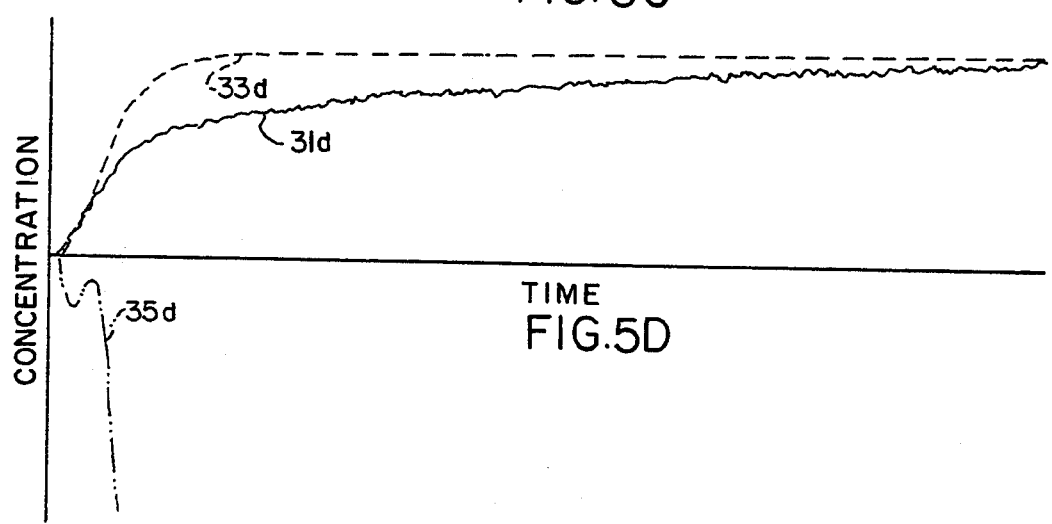

As shown in FIGS. 5a–5d, further in accordance with the present invention the ethanol concentration profile 31a–31d and carbon dioxide profile 33a–33d are offset to provide equal starting values, and the ethanol profile is scaled to provide equal ending values. This step is carried out mathematically so that both profiles share the same baseline value and maximum (plateau) value. The carbon dioxide profile 33 is then subtracted from the ethanol profile 31 to produce a third curve 35. In accordance with this preferred embodiment of the present invention, the third curve 35 represents the cumulative difference between the ethanol curve and the carbon dioxide curve. In FIG. 5a, with a subject who has ingested alcohol one minute before the test and has a large residual amount of alcohol in his upper respiratory tract, curve 35a extends well beyond the scale of the graph and would clearly identify mouth alcohol. Likewise in FIG. 5b, three minutes after alcohol ingestion, the curve 35b extends off scale. In FIG. 5c, five minutes after ingestion, the amount of mouth alcohol is considerably less, and a less pronounced peak 35c is produced; the peak is nonetheless identifiable as mouth alcohol. In FIG. 5d, showing a test made after an additional ten minutes, the curve 35d never becomes positive and extends off scale in the negative direction, indicating the absence of mouth alcohol.

Figure 6:
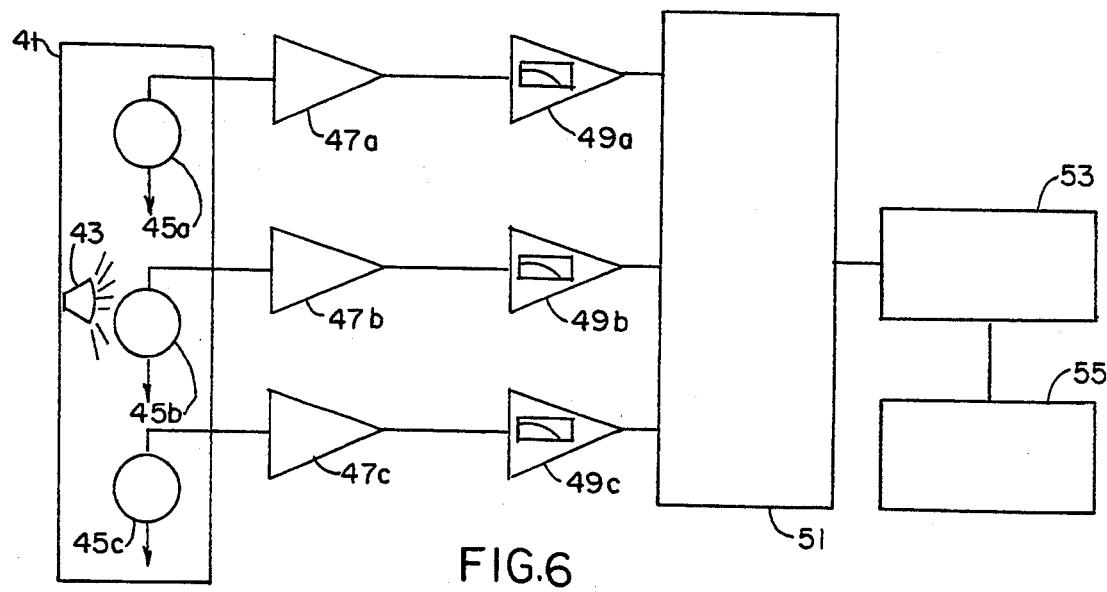
FIG. 6 is a diagrammatic representation of one illustrative embodiment of apparatus of the present invention for carrying out the method of the invention.

An instrument utilizing the method of the invention is shown diagrammatically in FIG. 6. The instrument is a modification of a standard infrared (IR) breath analyzer such as well-known commercially available analyzers or the device described in Fritzlen et al., U.S. Pat. No. 4,268,751, for example. Reference numeral 41 indicates an infrared IR cell through which a breath sample is continuously passed. In the cell, electromagnetic energy generated by an IR source 43 is absorbed by molecules of alcohol, carbon dioxide, and other substances before reaching three infrared detectors 45a, 45b and 45c at the other end of the cell 41. The detectors 45 are thermopile type IR sensors. Each detector 45 has a different band pass filter that passes a narrow band of the spectrum. The ethanol channel 45a is filtered at and about 3.45 microns; the reference channel 45b is filtered at and about 4.82 microns, and the carbon dioxide channel 45c is filtered at and about 4.26 microns. Because the output of each detector is very small (on the order of hundreds of microvolts), each channel is amplified by a factor of 26,000 by operational amplifiers 47a, 47b, and 47c, respectively. After amplification, the signals are passed through filters 49a, 49b, and 49c respectively to remove noise. Each filter 49 is a multi-pole, low pass active filter which attenuates frequencies above 10 HZ. Each channel is then passed to an analog to digital converter 51 which samples each channel at a rate of sixty times per second and converts each signal into a digital representation. These digital signals are then processed numerically by a microprocessor 53.

The outputs of all three channels are monitored constantly, and the reference channel is factored out from the ethanol and carbon dioxide signals in order to produce the respective output curves. The diminishment of signal from each detector is measured to determine the concentration of alcohol and carbon dioxide present at a given point in time, in accordance with Beer's law:

$C = (\ln(I_0 / I_i)) / (a * x)$, where $I_0$ = reference signal $I_i$ = measured gas signal ($CO_2$ or EtOH).

a = calibration constant x = path length, and

C = concentration of carbon dioxide or ethanol.

The numerical concentration values for each gas for the entire measurement are stored. Any difference between the initial alcohol and carbon dioxide values and zero is subtracted for each numerical concentration value. At the end of the measurement, the maximum (plateau) carbon dioxide value for the measurement are compared with the maximum (plateau) alcohol value for the measurement, to determine a ratio. All the alcohol values are then multiplied by this ratio to normalize the alcohol and carbon dioxide values. Finally, the carbon dioxide values are sequentially subtracted from the corresponding normalized alcohol values, and difference is added to an accumulator. If the value in the accumulator (representing the curve 35) during a predetermined part of the profile exceeds a predetermined threshold, the signal is sent to display 55, to show that mouth alcohol is present. In the preferred embodiment, the accumulator value must exceed the threshold within 1.5 seconds of detection of alcohol in order to trigger the display 55. The value of the threshold is set empirically, to account for such variables as alcohol in the saliva of the subject; it must be kept small enough to detect and signal an amount of mouth alcohol which would interfere with an accurate and reliable blood alcohol (alveolar alcohol) determination. If desired, the value of the largest number in the accumulator (the peak of the curve 35) may be stored and displayed, to indicate the magnitude of mouth alcohol.

Numerous variations in the method and device of the invention, within the scope of the appended claims will occur to those skilled in the art in light of the foregoing disclosure. Merely by way of example, averaging later alcohol and carbon dioxide measurements (representing the plateau values of the gases) before normalization tends to filter the values and provide more consistent results. Many well-known techniques may be used in constructing the infra-red sensor system and processing the outputs of the sensors, including for example methods of determining the overall characterization of the subject's exhalation, methods of detecting non-alcoholic constituents of breath, and methods of determining the end point of the determination. Other alveolar gases such as water vapor could be detected. Other sensors than the preferred IR sensor may be used, such as the filament sensor used by Kiefer et al., U.S. Pat. No. 3,830,630 to distinguish alcohol and carbon dioxide in breath. These variations are merely illustrative.

We claim:

1. A method for determining the presence of upper respiratory alcohol in a breath sample continuously delivered to a sensing device, said method comprising:

a step of taking a plurality of measures of alcohol and an alveolar gas over a period of time, initial measures of said alcohol and alveolar gas representing upper respiratory breath and later measures representing deep lung breath, a step of normalizing said plurality of alcohol and alveolar gas measures to produce equal alcohol and alveolar gas measures representing deep lung breath, a step of comparing the normalized alcohol and alveolar gas measures representing at least upper respiratory breath, and determining from the compared alcohol and alveolar gas measures whether upper respiratory alcohol was present in the breath sample.

2. The method of claim 1 wherein said alveolar gas is carbon dioxide.

3. The method of claim 1 further including a step of producing a signal if the step of comparing normalized alcohol and alveolar gas measures produces a value above a predetermined threshold value.

4. The method of claim 3 wherein said comparing step includes determining differences between said plurality of normalized alcohol and alveolar gas measures.

5. The method of claim 3 wherein said comparing step includes a step of summing a plurality of differences between said normalized alcohol and alveolar gas measures.

6. The method of claim 5 wherein said step of summing a plurality of differences between said normalized alcohol and alveolar gas measures comprises comparing said summed differences with said threshold value during a predetermined period of time.

* * * * *